United States Patent

Wakabayashi et al.

[11] Patent Number: 5,090,232
[45] Date of Patent: Feb. 25, 1992

[54] METHOD AND APPARATUS FOR DETECTING ODORS

[75] Inventors: Yasusuke Wakabayashi, Kurume; Takeo Koizumi, Yokohama; Katuo Ehara, Tokyo; Masataka Hara, Kurume; Masahiro Ehara, Jojima, all of Japan

[73] Assignee: Wakabayashi & Co., Kurume, Japan

[21] Appl. No.: 523,809

[22] Filed: May 16, 1990

[30] Foreign Application Priority Data

May 19, 1989 [JP] Japan ................................ 1-127694

[51] Int. Cl.⁵ ................................................ G01N 31/00
[52] U.S. Cl. ................................... 73/23.34; 73/1 G
[58] Field of Search ................ 73/23.34, 1 G, 31.02, 73/31.06, 23.2; 422/88, 98

[56] References Cited

U.S. PATENT DOCUMENTS

| | | | |
|---|---|---|---|
| 4,240,799 | 12/1980 | Ryerson | 73/31.02 |
| 4,563,893 | 1/1986 | Tanyolac et al. | 73/31.05 |
| 4,770,027 | 10/1988 | Ehara et al. | 73/23.34 |
| 4,884,435 | 12/1989 | Ehara | 73/23.34 |

Primary Examiner—Hezron E. Williams
Attorney, Agent, or Firm—Jones, Tullar & Cooper

[57] ABSTRACT

The invention involves the detection of odors using an odor detector including an n-type semiconductor sensor having an electric resistance responsive to odor molecules adsorbed thereonto. An ozonizer is provided within a test compartment to contact the detector with an ozone gas for the purpose of calibrating the detector to an initial zero setting. The test compartment also includes a ventilation fan operable to draw purging air into the compartment. In order to minimize the time required to bring the detector to the initial zero setting, a computer is used to selectively actuate the ozonizer and the ventilation fan in a controlled manner. Before starting a new detection cycle, an operator selects a specific table of optimal pattern for quick recovery to the zero setting from among a plurality of tables stored in the computer, based on certain factors such as the identity and concentration of previously detected odorant substances, etc.

4 Claims, 4 Drawing Sheets

METHOD AND APPARATUS FOR DETECTING ODORS

BACKGROUND OF THE INVENTION

1. Field of the Invention

This invention relates to odor detectors and, more particularly, to a method and apparatus for shortening the time required to bring such an odor detector to a predetermined initial setting for the next detection cycle by purging a detection chamber containing the odor detector through a controlled operation of an ozonizer and a ventilation fan. In this invention, a plurality of tables may be provided for use with a computer to enable a rapid and efficient recovery of detector readings to the initial setting by reference to a specific table which is selected by an operator from among the tables depending upon certain factors including the identity and concentration of previously detected odorant substances.

2. Description of the Prior Art

Odorimetry plays an important role in the field of quality inspection. For example, objective odor determination can be made in the food processing industries, where the freshness and the quality of comestible products can be determined objectively through use of various odor detectors. An odor detector could also have many other applications such as control of fermentation, analysis of raw materials, testing of alcholic or other drug intoxication, etc. Likewise, there are many uses for such a device in the perfume and cosmetic industries. Gas chromatography has frequently been used for detecting the identity and concentration of odorant substances. This technique, however, has certain shortcomings: (1) Results of detection vary depending upon the particular sampling method used; (2) The detections have to be carried out by a person reasonably skilled in the test; (3) Apparatus useful in such gas chromatography is generally costly; and (4) It takes a considerable time before the results are given.

Various types of odor or gas detectors have been proposed and developed which are capable of reliably detecting minute concentrations of odorant substances. U.S. Pat. No. 4,770,027 to Ehara et al discloses one such arrangement which provides the total concentration of odors emitting from an object such as comestible products as an indication of its specific quality including freshness and maturity. In the U.S. patent, an n-type metal oxide semiconductor is utilized as a sensing means which is heated to a predetermined high operating temperature by an electric heater disposed adjacent thereto. The n-type semiconductor, when heated, is responsive to odor molecules absorbed thereonto. Adsorption of odor molecules will cause electrons to be exchanged between the molecules and the semiconductor surface to cause a change in the electron concentration in the semiconductor. The changing electron concentration varies the electric resistance of the semiconductor thus permitting an accurate determination of the total concentration of the odors.

In order to detect odorant substances using the detector of this type, it is necessary to bring the detector to an initial zero setting where the detector chamber is odorless, prior to starting a new detection cycle. Depending upon the identity and concentration of odorant substances, it usually takes ten to fifty minutes before such initial setting is attained. This will disadvantageously place a limitation on the number of detection cycles accommodated within a certain period of time. If odorant substances of high retentivity have been tested in the previous detection cycle or if a detection was made relatively close to a source of strong smell, the ambient air around the odor detector is "contaminated", or contains minute concentrations of such odors, which may require an unreasonably long time of recovery to the zero setting and sometimes make it impossible to restart detection cycles.

It is a principal object of this invention to provide an improved method and apparatus which enable repeated detections of odorant substances in a quick and efficient manner with a view to overcoming the above-stated shortcomings of the prior art.

It is another object of this invention to provide an improved method and apparatus which can shorten the time required to bring an odor detector to an initial zero setting for repeated and efficient detection of odorant substances.

Yet another object of this invention is to provide an improved method and apparatus which uses an ozonizer along with a ventilation fan to purge a detection chamber prior to the commencement of a new detection cycle.

It is a further object of this invention to provide an improved method and apparatus which utilizes a computer to coordinate ozone generation with activation of a ventilation fan in such a manner as to minimize the time it takes for the odor detector to return to an initial zero setting.

Yet a further object of this invention is to provide an improved method and apparatus in which an operator can select a specific table of optimal pattern for quick recovery to an initial zero setting for a subsequent detection cycle from among a plurality of tables stored in a computer.

SUMMARY OF THE INVENTION

The objects stated above and other related objects in this invention are accomplished by the provision of a method for detecting odors, comprising the steps of: providing an odor sensing means having an electrical property responsive to odor molecules adsorbed onto said sensing means; contacting said sensing means with an ozone gas by allowing the gas to pass through said sensing means; detecting the electrical property of said sensing means prior to exposing said sensing means to odorant substances, for the purpose of using the detected property value for an initial zero setting; exposing said sensing means to said odorant substances; and detecting the electrical property of said sensing means relative to said initial zero setting as an indication of the odors emitting from said odorant substances.

Further in accordace with the present invention, there is provided a method for detecting odors, comprising the steps of: providing a test compartment for accommodating odorant substances therein; providing an odor sensing means in said test compartment, said odor sensing means having an electrical property responsive to odor molecules adsorbed onto said sensing means; detecting the electrical property of said sensing means prior to placing a first sample of odorant substances within said test compartment, for the purpose of using the detected property value for an initial zero setting; placing said first sample of odorant substances within said test compartment; detecting the electrical property of said sensing means relative to said initial zero setting as an indication of the odors emitting from said first sample of odorant substances; removing said first sample of odorant substances from said test compartment; contacting said sensing means with an ozone gas by allowing the gas to pass through said sensing means until the electrical property of said sensing means returns to said initial zero setting; placing a second sample of odorant substances within said test compartment; and detecting the electrical property of said sensing means relative to said initial zero setting as an indication of the odors emitting from said second sample of odorant substances.

The present invention also contemplates an apparatus for the detection of odors, comprising: an odor sensing means having an electrical property responsive to odor molecules adsorbed onto said sensing means; means for contacting said sensing means with an ozone gas by allowing the gas to pass through said sensing means; means for calibrating said sensing means to an initial zero setting while being contacted with the ozone gas; means for exposing said sensing means to odorant substances; and means for detecting the electrical property of said sensing means relative to said initial zero setting as an indication of the odors emitting from said odorant substances.

Still further in accordance with the present invention, there is provided an apparatus for the detection of odors, comprising: a test compartment for accommodating odorant substances therein; an odor sensing means disposed within said test compartment, said odor sensing means having an electrical property responsive to odor molecules adsorbed onto said sensing means; means for generating an ozone gas in said test compartment and for allowing the generated ozone gas to pass through said sensing means so as to contact it; means for calibrating said sensing means to an initial zero setting while being contacted with the ozone gas; means for detecting the electrical property of said sensing means relative to said initial zero setting as an indication of the odors emitting from said odorant substances.

The odor sensing means comprises an n-type semiconductor having an electrical resistance responsive to odor molecules adsorbed thereonto. An ultraviolet lamp is utilized to generate the ozone gas.

A fan means is provided on the test compartment to draw purging air into the compartment. The fan means is operable in response to the electrical property of the sensing means overshooting the initial zero setting, thereby causing the electrical property to converge into the initial zero setting.

A computer is employed to cause the electrical property of the sensing means to converge into the initial zero setting by selectively contacting the sensing means with the ozone gas and the purging air in a controlled manner. The computer operates to cause the electrical property to converge into the initial zero setting by reference to a specific table which is selected by an operator from among a plurality of tables stored in the computer for quick return to the initial zero setting.

BRIEF DESCRIPTION OF THS DRAWINGS

The above, as well as other features and advantages of the invention, will become apparent through consideration of the following detailed description in connection with the accompanying drawings, in which.

BRIEF DESCRIPTION OF THE PREFERRED EMBODIMENTS

Figure 1:
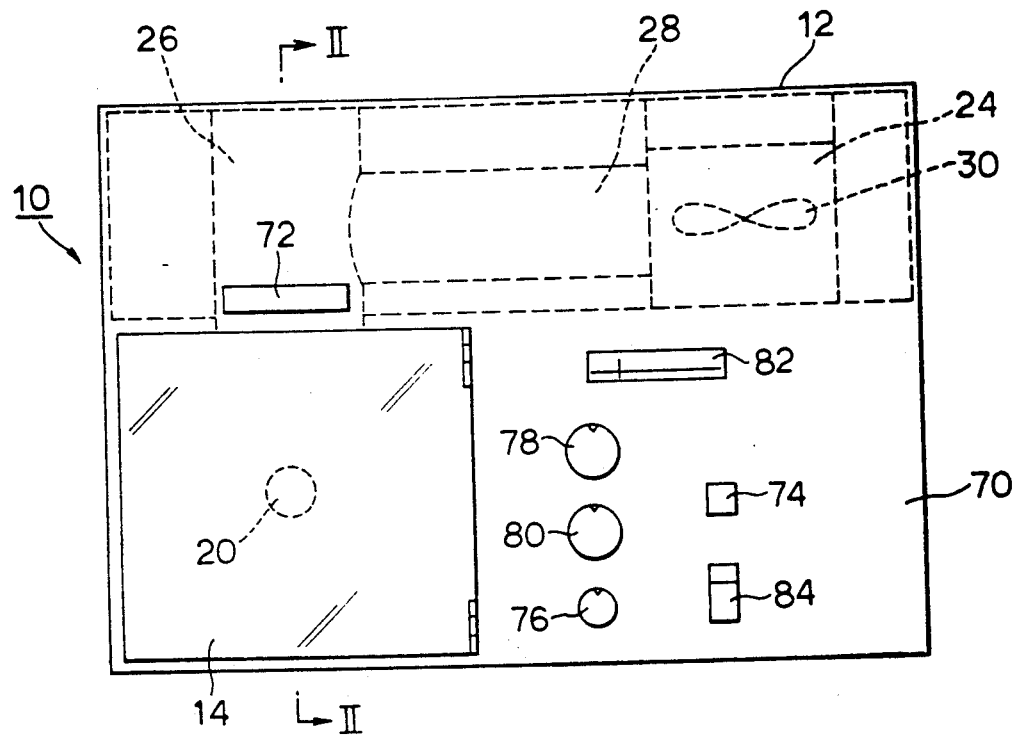
FIG. 1 is a front elevation showing an odor detector embodying the present invention.
Figure 2:
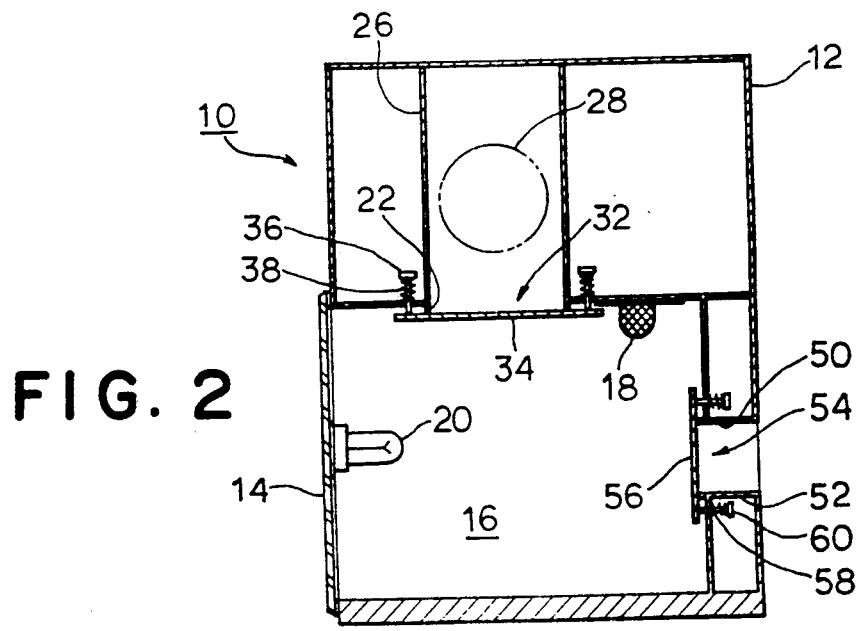
FIG. 2 is a side elevation of the odor detector shown in FIG. 1.
Figure 3:
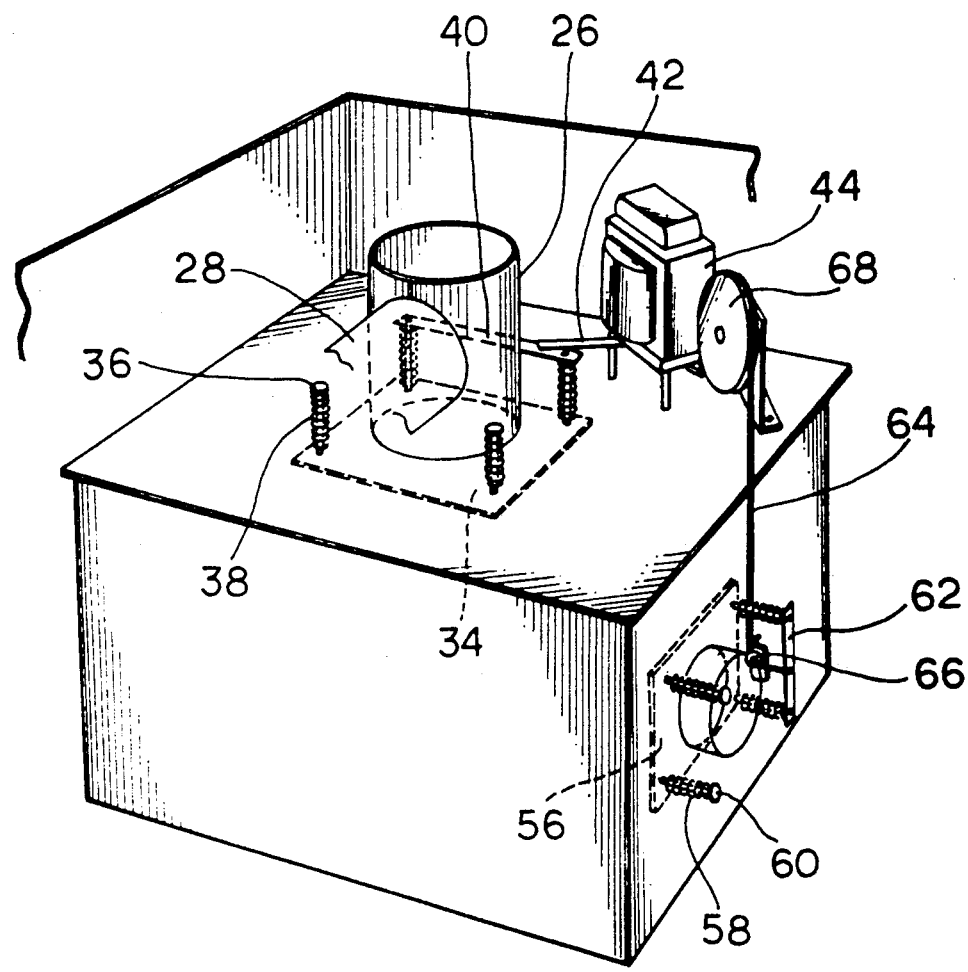
FIG. 3 is an exploded perspective view of the odor detector shown in FIGS. 1 and 2.

Referring now to the drawings, and particularly to FIGS. 1, 2 and 3, there is illustrated an odor detector of the present invention generally designated by the numeral 10. As shown, the odor detector 10 comprises a suitable housing 12 to house the several parts, to be detailed hereinafter. The housing 12 is provided with a hinged door 14 for access to a test compartment 16 defined in the housing 12. The door 14, when in the illustrated position, sealingly closes the test compartment 16 to isolate it from the surrounding atmosphere. Preferably, the test compartment 16 may be lined with stainless steel or other suitable anti-corrosive materials. A sensor 18 is provided on the ceiling of the test compartment away from the door 14.

In accordance with a preferred embodiment of the invention, the sensor 18 comprises a simple substance of an n-type metal oxide semiconductor such as sintered body of 99.999% pure tin oxide ($SnO_2$) containing $Al_2O_3$ as a binder. As an alternative, a 0.6 mm thick ceramic plate having a thin film of such a metal oxide deposited thereon by vacuum vapor deposition may be employed. A simple substance of n-type zinc oxide (ZnO) may also be used to form the sensor 18. Although not specifically shown, the sensor 18 has associated therewith a suitable electric heater for maintaining the sensor at a predetermined high, constant, operating temperature so that sensor readings may be independent of the temperature and humidity of the ambient air. The sensor 18 may not be required to have the capability of discriminating various kinds of odors but is sufficient to be able to give an indication of the total concentration of such odors. A plurality of like sensors having their characteristic curves staggered by maintaining the respective sensors at different temperatures may be used in place of a single sensor.

As best seen in FIG. 2, the odor detector 10 includes an ozonizer in the form of an ultraviolet lamp 20 which is provided on the back surface of the door 14. For this purpose, for example, an ultraviolet lamp manufactured under the designation of QGUL-11-65Z by Prince Electric Co., Japan, may be employed. In an alternate embodiment of the invention, it is possible to provide such an ultraviolet lamp outside the test compartment 16 such that after completion of one detection cycle, the sensor 18 may be removed from the compartment for exposure to the ultraviolet lamp outside thereof. The test compartment 16 is suitably formed to allow easy access for insertion and removal of an odor carrying object and is lined with stainless steel, as described above. The ceiling of the test compartment 16 is formed near its center with a purging gas or air inlet port 22. The air inlet port 22 is in communication with a ventilation fan compartment 16 through a vertically disposed cylindrical conduit 26 and a horizontally disposed cylindrical conduit 28 which are coupled to each other in an air-tight manner. Although not shown in FIG. 3 for clarity of illustration, a ventilation fan 30 is provided in the compartment 16 to draw the ambient air into the test compartment so as to purge it in the manner to be described later in more detail. Also, it is preferred that the vertically disposed conduit 26 includes a filter containing various absorbent materials such as activated charcoal, which are capable of irreversibly removing from the incoming air certain undesirable or interfering molecules.

The purging air inlet port 22 has associated therewith a first isolating valve 32 which, when closed, acts to prevent entry of the ambient air through the inlet port 22 into the test compartment 16. In the illustrated embodiment, the first isolating valve 32 comprises a generally square plate 34 which normally is horizontally disposed so as to seal off the lower circumferential end of the vertically disposed conduit 26 that extends slightly downward from the ceiling of the test compartment 16. The square plate 34 has provided near its corners four studs 36 which extend through holes formed in the compartment ceiling in a manner to surround the air inlet port 22. A coiled spring 38 is provided on each stud 36 between its head portion and the upper surface of the ceiling to normally bias the square plate 34 upwardly to close off the air inlet port 22. As best seen in FIG. 3, an operating link 40 is provided in a manner to connect the head portions of the two studs 36 and is operatively associated with a horizontally disposed operating rod 42 which forms a part of a solenoid device 44. The solenoid device 44, when actuated, acts to move the horizontally disposed operating rod 42 downwardly, causing the operating link 40 to move downwardly so as to move the square plate 34 away from sealing engagement with the air inlet port 22.

Referring back to FIG. 2, the test compartment 16 includes a purging gas or air outlet port 50 formed in the opposite inside surface to the door 14. Another horizontally disposed conduit 52 extends through the test compartment 16 and the back surface of the housing 12 to serve as the air outlet port 50. The air outlet port 50 has associated therewith a second isolating valve 54 which is similar in structure to the first isolating valve 32. A vertically disposed plate 56 is normally biased against the circumferential end of the conduit 52 by coiled springs 58 on four studs 60 extending from the plate 56, in a manner to seal off the outlet port 50. Another operating link 62 is provided which connects the head portions of two adjacent studs 60 and includes a wire 64 having one end secured to the operating link 62 at its midpoint. Two pulleys 66 and 68 are provided to operatively connect the operating link 62 to the solenoid device 44 by way of the wire 64. In this arrangement, the solenoid device 44, when actuated, acts to pull the wire 64 upwardly, causing the operating link 62 to move toward the back surface of the test compartment 16 so that the vertically disposed plate 56 is moved away from sealing engagement with the circumferential end of the conduit 52 to open the outlet port 50. It should be noted that, in the illustrated embodiment, the operations of the ventilation fan 30, the first and second isolating valves 32 and 54 are coordinated such that in response to an operator command, both of the isolating valves are moved to the open positions simultaneously with the activation of the ventilation fan to purge the test compartment 16 in an effective and efficient manner.

Referring back to FIG. 1, the housing 12 is provided with a control panel 70 which includes a display 72 for providing a digital reading of the electric current through the sensor 18 as an indication of the concentration of odors. A power switch 74 is provided for a suitable power supply (not shown) which may be self-contained or supplied from an external power line (not shown). Also shown on the housing 12 is a fan switch 76 which permits a selective activation of the ventilation fan 30. A control knob 78 is provided to vary the magnitude of the voltage to be applied to the sensor 18. Another control knob 80 is provided just below the knob 78 to enable a zero adjustment of the digital reading on display 72. Disposed above these control knobs is a voltmeter 82 for providing a reading of the voltage applied to the sensor. A knob 84 for holding a peak value of the concentration of odors as detected is also provided on the control panel 70.

Figure 4:
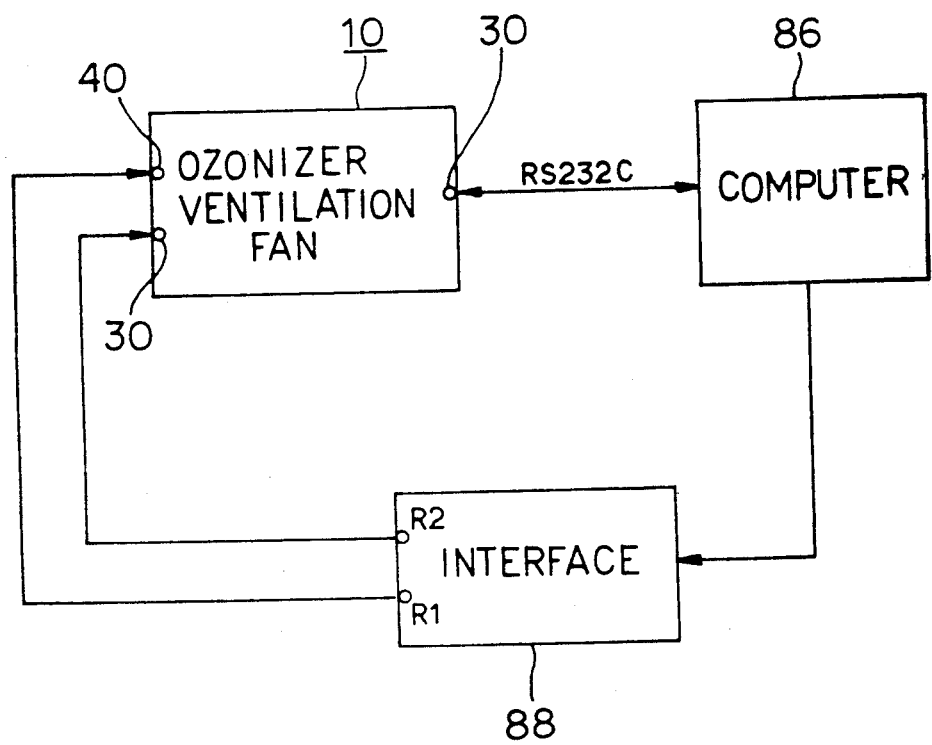
FIG. 4 is a simplified block diagram showing how the odor detector is brought to an initial zero setting using a computer.

FIG. 4 is a block diagram showing the exemplary hardware for controlling the atmosphere in the test compartment 16 so as to make the odor detector 10 ready to start a new detection cycle. As shown, the hardware includes a computer 86 which may take the form of a personal computer or a mini-computer. The computer 86 is coupled via an RS 232C cable to the sensor 18 to receive therefrom electric signals indicative of the operational status of the ozonizer and the ventilation fan. The computer is also connected to an interface 88 including relays R1 and R2 which are in turn connected to the ozonizer 20 and the ventilation fan 30, respectively. Command signals from the computer 86 will control the operations of the relays R1 and R2 which determine the operational status of the ozonizer and the ventilation fan.

In operation, the power switch 74 is turned "ON" and then the control knob 78 is manually adjusted to provide a predetermined voltage to the sensor 18, with the door 14 closed. This will start heating the sensor to a predetermined, constant operating temperature. The next step is to determine that the sensor current on the digital display 72 has become stable, which means that the semiconductor sensor 18 is now ready for operation so that the new detection cycle can start. The fan switch 76 is then actuated, which simultaneously causes the first and second isolating valves 32 and 54 to open, as described above. This will introduce the purging gas or air into the test compartment 16 to make the compartment odorless, enabling the odor detector 10 to be calibrated to a predetermined initial zero setting. Specifically, this calibration is accomplished by turning the control knob 80 for zero adjustment. It should be understood that it may not be necessary to purge the test compartment 16 with the purging air prior to commencing a first detection cycle. In this case, the detection cycle can be started immediately after the zero adjustment of the odor concentration reading on the digital display 72 is made.

Next, the door 14 is opened to place a sample of odorant substances in the test compartment 16, and the door 14 is closed to seal off the compartment. Gases carrying the odors start to fill the test compartment, coming into contact with the semiconductor sensor 18. Adsorption of the odorant substances will occur on the semiconductor sensor, causing the sensor to undergo an electric resistance change. The changing resistance alters the electric current through the sensor, causing a corresponding variation in the digital reading on the display 72. The peak value of the digital reading is proportional to the amount of adsorption taking place on the sensor, accordingly the total concentration of odors emitted from the sample.

Figure 5:
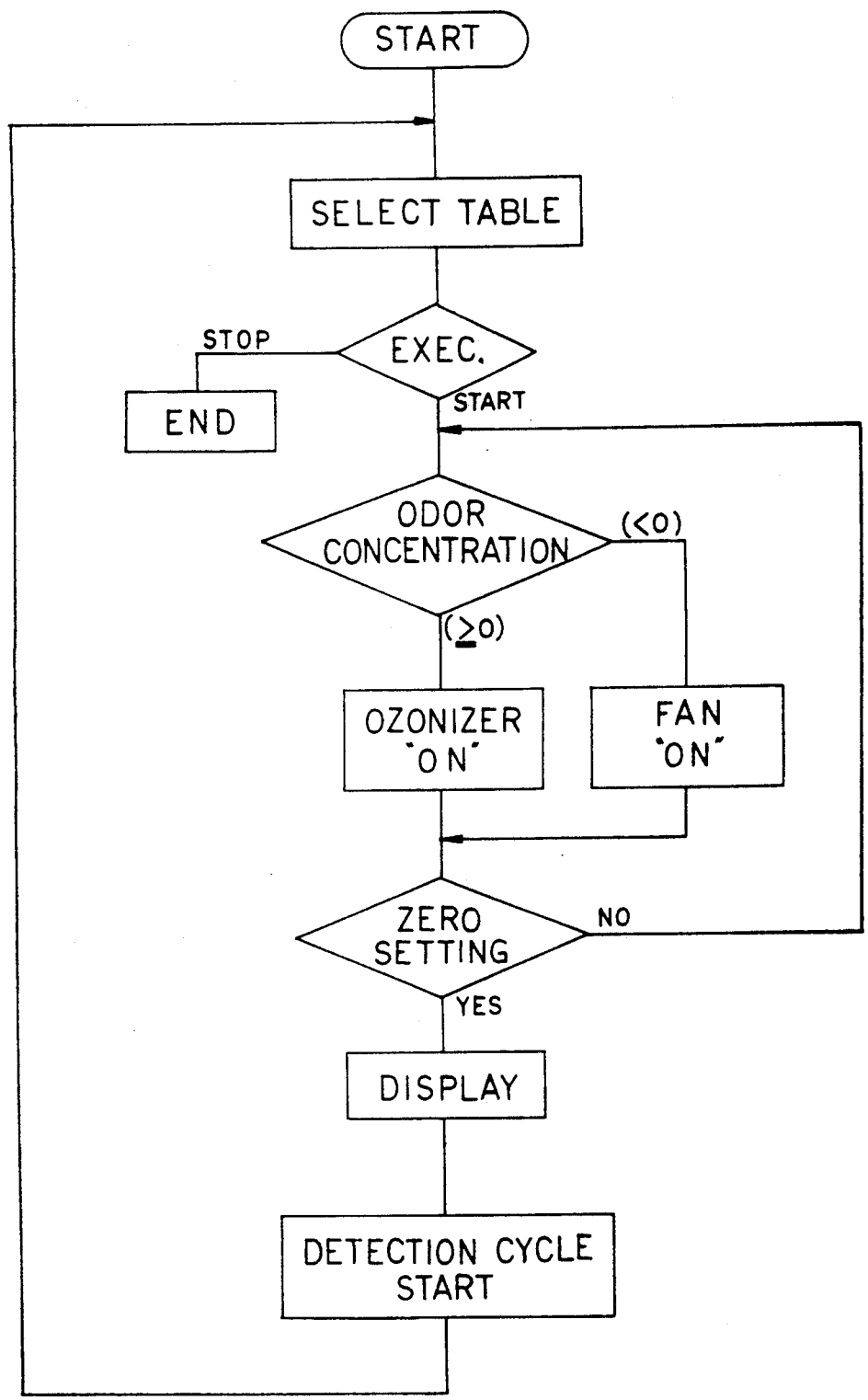
FIG. 5 is a flow diagram showing in more detail the manner of control shown in FIG. 4.

Once the detection cycle has been completed, an operator gives a specific command to the computer 86 to start the necessary procedure for bringing the odor detector 10 to the initial zero setting for subseqent detection. A flow chart of the steps performed by the computer 86 of FIG. 4 is illustrated in FIG. 5. As shown, the first step is to provide the start command to the computer 86, as described above. The next step is to select a specific table from among a plurality of tables stored in the computer memory (not shown), based on the identity and the peak concentration recorded from the previous detection cycle, the estimated rate of decrease of odor concentration toward the zero setting, the expected time interval between check points, the "ON" duration for the ultraviolet lamp 20, the ON duration for the ventilation fan 30, etc. The computer 86 is programmed to execute a series of steps in accordance with the specific software stored in the memory so as to bring the odor concentration in the test compartment 16 to the zero setting by periodically comparing the concentration reading with that specified by the selected table at every check point to selectively operate the ozonizer 20 and the ventilation fan 30. A typical example of a table by reference to which the atmosphere in the test compartment 16 is controlled into the zero setting is shown below:

| Odor Concentration | Rate of Decrease | Check Interval | UV Lamp Duration | Ventil. Fan Duration |
|---|---|---|---|---|
| >1800 | 4 (/sec.) | 30 (sec.) | 30 (sec.) | |
| >1600 | 4 | 30 | 30 | |
| >1400 | 4 | 30 | 30 | |
| >1200 | 4 | 30 | 30 | |
| >1000 | 4 | 30 | 30 | |
| >800 | 4 | 30 | 30 | |
| >600 | 4 | 30 | 30 | |
| >400 | 4 | 30 | 30 | |
| >200 | 4 | 30 | 30 | |
| >100 | 4 | 30 | 30 | |
| >50 | 4 | 30 | 30 | |
| >20 | 4 | 20 | 20 | |
| 0 | 4 | 20 | 20 | |
| <−20 | 2 | 20 | | 3 (sec.) |
| <−100 | 1 | 20 | | 3 |
| <−200 | 1 | 20 | | 5 |
| <−800 | 1 | 20 | | 5 |

As will be seen, the ultraviolet lamp 20 is generally maintained in an "ON" condition until the odor concentration decreases to the zero setting. This is accomplished by causing the relay R1 to be kept energized in response to a computer command. The ultraviolet lamp acts as an ozonizer to neutralize the odors remaining in the test compartment 16. If the ultraviolet lamp 20 is kept "ON" too long, it has been found that the odor concentration decreases below the zero setting. When this occurs, the computer 86 automatically gives a command to the interface 88 that causes the relay R2 to be energized to actuate the ventilation fan 30. It has been found through experimentation that introducing the purging air will cause the odor concentration in the compartment to increase toward the zero setting. Once the odor concentration has been returned to the zero setting, it will be appreciated that the odor detector 10 is ready to perform the next detection cycle.

It should be understood that in accordance with the preferred embodiment of the present invention, the odor detector can be brought to the initial zero setting in a minimum of time. The use of the ozonizer and the ventilation fan which are selectively activated depending upon the current concentration of odors from the previously tested odorant substances will result in a remarkable reduction in the time required to bring the detector to the zero setting. Furthermore, computer control of the atmosphere in the test compartment using a plurality of stored tables will contribute greatly to a quick return to the zero setting, which will accommodate more detection cycles within a certain period of time. The following table shows comparative data between the odor detector of the invention and a typical detector of conventional type, regarding the time required to bring the detector to the zero setting after a detection cycle of four minutes during which a particular sample was placed in the test compartment.

| | Time Required To Return To Zero Setting | |
|---|---|---|
| Sample | This Invention | Conventional Type |
| Soy Sauce | 4 mins. | 10 mins. |
| Ground Coffee | 6 mins. | 8 mins. |
| Adhesive | 10 mins. | 25 mins. |
| Ethanol | 10 mins. | 50 mins. |
| Aceton | 10 mins. | 60 mins. |

As will be seen, the present invention can shorten the time required to bring the odor detector to the zero setting, by the factor of ⅔ to 1/6 as compared to the conventional detector.

Although the present invention has been described in terms of what are at present believed to be its preferred embodiments, it will be apparent to those skilled in the art that various changes may be made without departing from the scope of the invention. It is therefore intended that the appended claims cover such changes.

What is claimed:

1. A method for detecting odors, comprising the steps of:

providing a test compartment for accommodating odorant substances therein;

providing an odor sensing means in said test compartment, said odor sensing means having an electrical property responsive to odor molecules adsorbed onto said sensing means;

detecting the electrical property of said sensing means prior to placing a first sample of odorant substances within said test compartment, for the purpose of using the detected property value for an initial zero setting;

placing said first sample of odorant substances within said test compartment;

detecting the electrical property of said sensing means relative to said initial zero setting as an indication of the total concentration of the odors emitting from said first sample of odorant substances;

removing said first sample of odorant substances from said test compartment;

contacting said sensing means with an ozone gas by allowing the gas to pass through said sensing means until the electrical property of said sensing means returns to said initial zero setting;

contacting said sensing means with purging air rather than the ozone gas if the electrical property of said sensing means overshoots the initial zero setting, thereby causing the electrical property to converge into the initial zero setting;

said ozone gas and said purging air contacting steps being selectively carried out by using a computer which operates to cause the electrical property of said sensing means to converge into said initial zero setting by reference to a specific table which is selected by an operator from among a plurality of tables stored in the computer for quick return to said initial zero setting, based on known factors including a peak concentration of said first sample, the estimated rate of decrease in the peak odor concentration toward the initial zero setting, the time during which said ozone gas is caused to contact the sensing means and the time during which said purging air is caused to contact the sensing means;

placing a second sample of odorant substances within said test compartment; and detecting the electrical property of said sensing means relative to said initial zero setting as an indication of the odors emitting from said second sample of odorant substances.

2. The method of claim 1 wherein said sensing means comprises an n-type semiconductor having an electrical resistance responsive to odor molecules adsorbed thereonto.

3. The method of claim 1 wherein said ozone gas is generated by an ultraviolet lamp.

4. The method of claim 1, further comprising the step of:

periodically comparing the sensed odor concentration with the peak concentration specified by said specific table to selectively carry out said ozone gas contacting step and said purging air contacting step on the basis of results of the comparison.

* * * * *